United States Patent [19]

Frankenberger et al.

[11] 4,207,160
[45] Jun. 10, 1980

[54] MEASURING SENSOR HEAD FOR DETERMINING THE CONTENTS OF GASES IN LIQUIDS

[75] Inventors: Horst Frankenberger, Bad Schwartau; Dieter Heller, Lübeck; Georg Ullrich, Freiburg im Breisgau, all of Fed. Rep. of Germany

[73] Assignee: Hellige GmbH, Freiburg im Breisgau, Fed. Rep. of Germany

[21] Appl. No.: 805,704

[22] Filed: Jun. 13, 1977

[30] Foreign Application Priority Data

Jun. 24, 1976 [DE] Fed. Rep. of Germany ....... 2628288

[51] Int. Cl.² .............................................. G01N 27/46
[52] U.S. Cl. ................................................. 204/195 P
[58] Field of Search ............................. 204/1 P, 195 P

[56] References Cited
U.S. PATENT DOCUMENTS

| | | | |
|---|---|---|---|
| 3,211,638 | 10/1965 | Halvorsen | 204/195 P |
| 3,380,905 | 4/1968 | Clark | 204/195 P |
| 3,415,730 | 12/1968 | Haddad | 204/195 P |
| 3,718,567 | 2/1973 | Haddad et al. | 204/195 P |
| 3,758,398 | 9/1973 | Doniguian | 204/195 P |

*Primary Examiner*—T. Tung
*Attorney, Agent, or Firm*—Norman E. Brunell; W. R. Thiel

[57] ABSTRACT

A measuring sensor head for determining the contents of gases in liquids, particularly for transcutaneous determination of oxygen in blood, as well as a method of manufacturing such sensor head are disclosed. In accordance with the invention, the gas-permeable membrane which covers the front face of the sensor head and which, during use, is applied to the human skin, is pre-shaped to assume a cap-shaped configuration. This eliminates previously occurring measuring errors due to uncontrollable stresses causing thickness variations generated in conventional membranes and, moreover, provides for an improved sealing effect between the housing of the measuring head and the membrane.

8 Claims, 2 Drawing Figures

MEASURING SENSOR HEAD FOR DETERMINING THE CONTENTS OF GASES IN LIQUIDS

FIELD OF THE INVENTION

This invention relates to electrochemical electrodes utilizing permeable membranes and, in particular, relates to measuring sensor heads used for electrochemically determining the contents of gases contained in media, preferably liquids, such as blood, and whose electrochemical measuring system is isolated therefrom by a membrane which is permeable for the gas to be measured.

DESCRIPTION OF THE PRIOR ART

The measuring system to be used can be an electrode system for the polarographic determination of oxygen, for example that developed by Clark, of which an improved form is described by Gleichmann and Lübbers (see U. Gleichmann and D. W. Lübbers, Pflügers Arch.ges. Physiol. 271:431...455 (1960)). Various modifications of such electrode systems have been described, for example by Lübbers and others (see Progr. Resp. Res. 3:136...146 (1969)). The concept of the present invention is especially applicable to those modifications which are brought into contact with the surface of the human body (see N. T. S. Evans and P. F. D. Naylor, Progr. Resp. Res. 3:161...164 (1969)). Such polarographic measuring sensors permit measuring the partial oxygen pressure in blood through the skin, i.e. transcutaneously (see R. Huch, D. W. Lübbers, A. Huch in Kessler u.a., *Oxygen Supply*, pp. 101...103b München-Berlin-Wien (1973)). The invention is described below, in the form of one embodiment of such polarographic measuring sensor head.

During use, a predetermined voltage is applied between the electrodes of such measuring sensor head, namely between the anode and one or several cathodes, which are surrounded by an electrolyte. As a result, the available oxygen is reduced due to the attraction of electrons, and the measuring current thus initiated will increase with an increasing number of reduced oxygen molecules. The number of oxygen molecules available at the surface of the cathode, all of which are reduced if the voltage is correctly adjusted, is a function of the oxygen flow which occurs to the cathode as the result of diffusion. This oxygen flow depends upon the difference in partial oxygen pressures at the cathode surface and in the measuring medium, i.e. the blood being investigated, and of the diffusion resistance therebetween. Since the partial oxygen pressure upon the cathode surface would be zero under the condition of reduction of all oxygen molecules, the measuring current becomes proportional to the partial oxygen pressure in the measuring medium and further depends upon the thickness of the layers of electrolyte and those properties of the diffusion membrane which are responsible for the resistance to diffusion. In connection with polarographic measuring equipment and sensors of this type, the last-mentioned conditions must be well reproducible and constant, in order to ensure uniform and constant measuring sensitivity.

The specific conditions with such polarographic measuring sensor heads are associated with certain requirements as to the nature and the shape of the diffusion membrane. The membrane must, on one side, prevent the electrolyte from flowing outwardly and it must also electrically isolate the electrode system from the measuring medium, actually the skin of a human body. However, on the other side, the membrane must permit the gas to be measured, for example oxygen, to reach the electrolyte and the cathode. Substances which can be used for such membranes are artificial materials, such as polypropylene, polyethylene, polytetrafluoroethylene, polyester, silicone rubber and others. This membrane must be removed from time to time, but it is highly desirable that this can be done without modifying the measuring properties of the sensor head. The means for securing the membrane to the sensor head must form such a tight seal that no electrolyte bridge to any surrounding medium, such as the human skin, can be formed.

In accordance with the conventional method for producing membranes for use with measuring sensor heads, the necessary pieces of film material have been cut out or punched out. Then, such piece was pulled over the front surface of the measuring sensor head and secured by means of a fastening ring. The film material which extended beyond the ring was cut off. Inasmuch as the geometric, i.e. spatial, structure of the measuring sensor head requires a stabilizing membrane for the purpose of stabilizing the layer thickness of the electrolyte between the diffusion membrane and the cathode, a stabilizing membrane has been interposed therebetween. Such stabilizing membrane must be permeable for the electrolyte, so that useful substances therefor include synthetic cellulose products, polypropylene and grid-, felt- or fabric-type structural materials.

Tests have shown that this method, when performed in this manner, does lead to only incomplete sealing between the electrode system and the measuring medium, inasmuch as this manner of application results in distorting tensions within the diffusion membrane whose thickness is thereby changed in a manner which cannot be controlled. The lack of a properly formed seal results in premature drying out of the electrochemical measuring system and in an undesired conductive connection to the surrounding medium. This is due to the fact that the conventional producing method causes the formation of pleats of the membrane material in the area to be sealed which leads to unavoidable lack of achieved sealing effect. Attempts to remedy this situation by subsequently deforming the membrane when pulling it over the measuring sensor head lead to more pronounced changes of membrane thickness, associated with uncontrollable modifications of measuring sensitivity of the sensor. Mechanical devices for pulling the membrane over the measuring head as uniformly as possible and without pleats did not prove to be satisfactory, as they did not lead to the desired result.

SUMMARY OF THE INVENTION

The present invention has therefore for its principal object the avoidance of the shortcomings associated with conventional membrane production and the conventional method of pulling the membrane over the measuring head, having particularly in view the prevention of the formation of pleats and irregularly occurring tensions and the different thicknesses of membrane associated therewith in the various areas of tension. Moreover, the invention has for its object the formation of a complete seal for the electrolyte where the diffusion membrane is to be secured to the housing of the sensor head.

In accordance with a broad aspect of the invention, it is seen to provide a measuring sensor head for determining the gas contents in liquids, particularly for the transcutaneous determination of gas contents in blood in accordance with a polarographic method, the sensor head having electrodes and an electrolyte in a hollow housing and a preformed cap-shaped sealing structure including a gas permeable membrane as its bottom portion for contact with the electrolyte and a rim portion sized to fit snugly around the outer peripheral surface of the head. The sealing structure is preformed, that is, the structure is formed into a cap shape before association with the housing.

In accordance with a different aspect of the invention, a method for manufacturing a measuring sensor head for determining the gas contents in liquids, particularly for the transcutaneous determination of gas contents in blood in accordance with a polarographic method is provided, which method comprises mounting an electrode assembly and an electrolyte within a housing for the sensor head, preforming a cap-shaped sealing structure whose bottom portion constitutes a gas-permeable membrane and assembling the structure with the housing.

BRIEF DESCRIPTION OF THE DRAWINGS

The invention will now be further explained with reference to the drawings, of which FIG. 1 schematically illustrates one embodiment of the invention, in the form of a measuring sensor head for operation in accordance with polarographic gas determination methods, when ready for use.

DETAILED DESCRIPTION OF THE PREFERRED EMBODIMENT

Figure 1:
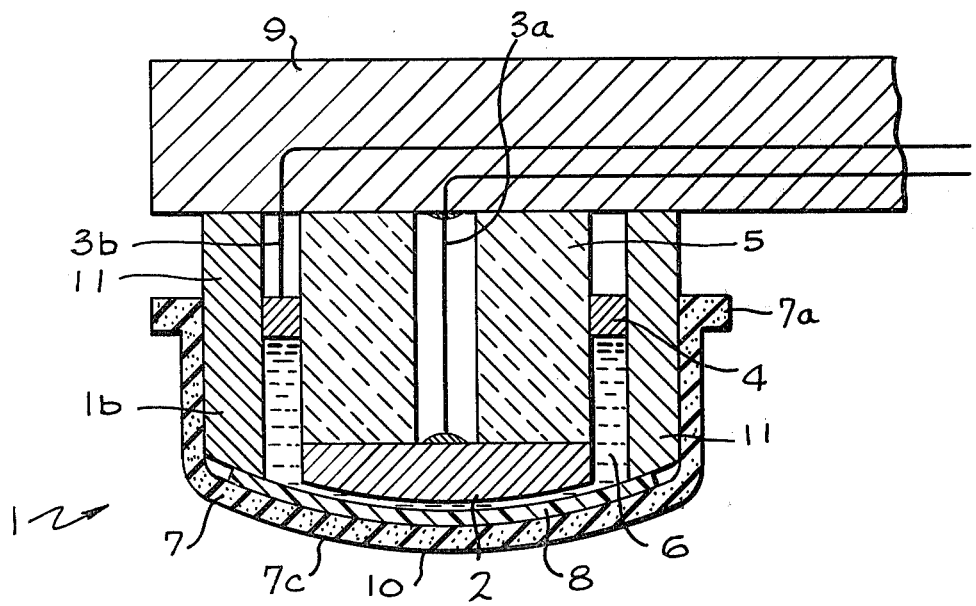

A measuring sensor head 1 with a flat or slightly curved front surface 10, as needed for the transcutaneous determination of the concentration of gases within blood by application to the skin, has a usually cylindrical or cubical housing 11. The head is secured to a support 9 which also accommodates electrical connections to the electrodes. Internally of the head 1 is disposed a cylindrical body 5 made of electrically insulating material, such as glass or plastic, which has applied to its front surface the cathode 2 made, for example, from platinum. The cathode connection line is indicated at 3a. A ring-shaped space is provided for accommodating the electrolyte 6, which surrounds the internal cathode 2, so that the cathode is in contact with the electrolyte. The other electrode, which is the anode 4, may be ring-shaped and provided at the upper boundary of the space for the electrolyte 6. Its electrical connection is shown at 3b.

The dimensions of measuring heads of the type contemplated lie between a few millimeters and one to two centimeters. For purposes of use in connection with transcutaneous methods, pointed electrode heads are not suitable, inasmuch as rather those with flat or flatly curved front surfaces are needed.

A sealing structure including a gas-permeable bottom portion, such as diffusion membrane 7, which is permeable for the gas to be determined, is shown in FIG. 1 when assembled with the measuring sensor head 1.

Figure 2:
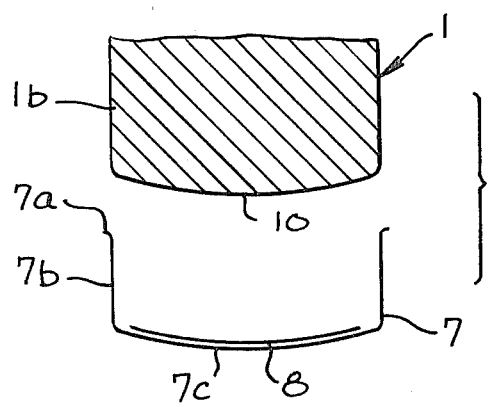
FIG. 2 is a simplified showing of the measuring sensor head of FIG. 1, when still separated from the membrane.

In accordance with the invention, this membrane 7 has been previously shaped, i.e. preformed, to assume a cup-, pot- or cap-shaped configuration by any suitable process, so that the lateral wall or rim portions 7b shown in FIG. 2 of the membrane are already, i.e. prior to assembly, shaped such that a snug fit with the head 1 of the measuring sensor is achieved, inasmuch as the wall portions 7b are configured to be complementary of the lateral or outer peripheral surface areas 1b of the head 1 to be covered by the membrane. Thus, it can be seen that the invention includes the method of manufacturing a measuring sensor head of the type described, the method comprising the step of separately forming the cap-shaped membrane and only subsequently assembling it with the housing of the head.

In order to prevent direct contact between the membrane 7, particularly its bottom portion 7c, and the front surface of the cathode 5, a stabilizing plate or film 8 is shown interposed therebetween, which is permeable for, or susceptible of impregnation by, the electrolyte 6 and also for the gas to be determined. The plate 8, which is thus seen to perform the function of a spacer, ensures that the electrolyte and the gas to be determined can come into contact with the cathode surface, the gas forming this contact after diffusion through the membrane 7. If desired, the plate 8 and the membrane 7 may form a single, integral unit.

It has been found particularly suitable if, in accordance with the invention, the front, i.e. lower, surface of the cathode 2 and the lower rim of the sensor housing 11 cooperate to form a slightly convex, continuously curved, i.e. vaulted, surface whose radius of curvature is somewhat shorter than the radius of curvature of the bottom portion 7c of the diffusion membrane 7 as preformed, but not yet joined to the measuring sensor head, this bottom portion 7c of the membrane in the preformed condition being suitably even completely flat for all practical purposes. When applying the membrane to the measuring sensor head housing 1, with the stabilizing plate 8 interposed, a slight tension is created within the membrane 7, of necessity, but such tension is necessary and sufficient to prevent subsequent uncontrollable changes in distance between the internal surface of the membrane and the lower, curved surface of the cathode 5, so that important parameters which may influence the measuring accuracy remain practically unchanged. If, moreover, the internal diameter of the rim area 7b of the membrane serving for securing it to the housing 11 is somewhat shorter than the external diameter of the housing 11 of the sensor, the tension within the membrane prevailing upon assembly is sufficient to ensure a perfect seal and to fixedly assemble the membrane 7 with the measuring sensor head, so that conventional, additional securing rings of rubber may be omitted. The securing effect can still be improved by providing a reinforcement in the form of the upper rim 7a of the membrane 7 forming a ring or collar, so that this rim, itself, supplies the tension necessary for the purpose of securing the membrane to the head.

The measuring sensor head, as constructed and manufactured in accordance with the invention, particularly for the transcutaneous determination of partial pressures of gases, such as $O_2$, $H_2$ and $CO_2$, within blood by means of polarographic measuring methods, contributes advantageously to the accuracy and the reproducibility of measurements, which constitutes an important progress in the art, as far as the application in practice and handling are concerned.

What is claimed is:

1. An improved sensor head of the type having a hollow sensor housing,
electrodes within said housing, and
an electrolyte in contact with said electrodes, wherein the improvement comprises:
a gas-permeable membrane mounted on said housing preformed into a cap shape having a rim portion integral therewith smaller in diameter than the outer peripheral surface of the housing so that the membrane fits snugly thereon and a bottom portion for contact with the electrolyte.

2. The improved sensor head as claimed in claim 1, wherein the electrodes are mounted in the sensor housing to form a convexly curved front surface and wherein, prior to assembly of the membrane with the housing, the curvature of said front surface exceeds the curvature of said bottom portion.

3. The improved sensor head as claimed in claim 2, wherein said bottom portion is flat prior to assembly with said housing.

4. The improved sensor head as claimed in claim 2, further comprising:
a spacer permeable to the electrolyte mounted and contained between the bottom portion and said front surface.

5. The improved sensor head as claimed in claim 4, wherein said bottom portion and said spacer constitute a single unit.

6. The improved sensor head as claimed in claim 1, wherein the improvement further comprises:
collar means integral with the membrane.

7. An improved measuring sensor head for determining gas contents in liquids of the type having an electrolyte and electrodes internally of the head and sealed off by a gas-permeable membrane mounted on said measuring head,
the improvement comprising an annular rim integral with the edge of said membrane, said rim being shaped to form, together with said membrane, a preformed cap-shaped, gas-permeable sealing structure smaller in diameter than the peripheral surface of said measuring head so that the membrane fits snugly thereon.

8. A method of manufacturing a sensor head, comprising:
mounting an electrode assembly and an electrolyte within a housing;
separately forming a gas-permeable membrane into a cap shape having a rim portion smaller in diameter than the outer peripheral surface of the housing; and
assembling said cap-shaped membrane with said housing so that the membrane fits snugly thereon.

* * * * *